United States Patent [19]
Itil et al.

[11] Patent Number: 4,800,888
[45] Date of Patent: Jan. 31, 1989

[54] ENHANCED ELECTRODE HEADSET

[75] Inventors: Turan M. Itil, Nyack; Donald M. Shapiro, Kings Point; Emin Eralp; Nils E. Johansson, both of Tarrytown, all of N.Y.

[73] Assignee: HZI Research Center Inc., Tarrytown, N.Y.

[21] Appl. No.: 86,616

[22] Filed: Aug. 17, 1987

[51] Int. Cl.$^4$ .............................................. A61B 5/04
[52] U.S. Cl. .................................. 128/644; 128/731; 128/791; 128/802
[58] Field of Search ................... 128/639, 642–644, 128/802, 731–732, 791

[56] References Cited

U.S. PATENT DOCUMENTS

| | | | |
|---|---|---|---|
| 2,208,023 | 7/1940 | Ellis | 128/639 |
| 3,735,753 | 5/1973 | Pisarski | 128/644 |
| 4,683,892 | 8/1987 | Johansson et al. | 128/639 |

FOREIGN PATENT DOCUMENTS

| | | | |
|---|---|---|---|
| 2124704 | 11/1972 | Fed. Rep. of Germany | 128/644 |
| 0225333 | 7/1985 | Fed. Rep. of Germany | 128/644 |
| 0676273 | 7/1979 | U.S.S.R. | 128/644 |
| 1168195 | 7/1985 | U.S.S.R. | 128/644 |

*Primary Examiner*—Kyle L. Howell
*Assistant Examiner*—Angela D. Sykes
*Attorney, Agent, or Firm*—Evelyn M. Sommer

[57] ABSTRACT

An electrode assembly is mounted in a helmet like headset for use in making multiple electrode contact with the scalp. Each electrode assembly includes an electrode that floats in a cylinder mounted in a pressure responsive drive, which, when under pressure carries the electrode toward the scalp of a patient wearing the headset. Mounted in the cylinder above the electrode and biased away from the electrode is an LSI chip carrying an operation amplifier and a power supply for the amplifier. When the electrode makes contact with the scalp the cylinder continues to drive forward. Back pressure from contact with the scalp overcomes the bias and completes a circuit to turn on the amplifier. The amplifier is connected via wire or a wireless signal transmit system to a computer into which amplified signals are fed.

10 Claims, 2 Drawing Sheets

ENHANCED ELECTRODE HEADSET

BACKGROUND OF THE INVENTION

The present invention relates generally to improved methods and apparatus for conducting brain function diagnosis and testing and, more particularly to improved apparatus which can be used for accurately measuring a subject's brain waves during electroencephalography testing.

An electroencephalograph machine, commonly referred to as EEG, is a multi-channel clinical instrument used to detect, measure and display electrical impulses or brain waves of a subject. The brain waves, which are electrical impulses generated by billions of neurons in the brain are detected and monitored during EEG testing by the use plurality of individual electrodes which are adapted to make contact with the subject's scalp in a predetermined pattern or montage, which is well known in the art. Electrical impulses generated by the subject's brain are detected by the electrodes and are transmitted to external monitoring and display devices. The character of the impulses so detected are displayed on a paper stripchart and/or tape and/or displayed on a screen for viewing and diagnostic study and interpretation.

In the prior art, early EEG testing included the display of representations of brain waves or impulses using multi-channel recording devices in which the impulses detected by each electrode were represented as traces scribed on a paper stripchart or tape by a galvanometer type instrument. More updated equipment employs the use of microcomputers into which brain waves detected by the electrodes are applied, and, in accordance with a prerecorded program, are analyzed and displayed for instant visual observation on a CRT and preserved on tape or other magnetic or optical means for more intense observation and study.

Computers used in conjunction with EEG testing, in some cases automatically record and analyze brain waves detected by the electrodes of the EEG and, in more advanced computer systems, prepare detailed reports on the brain waves detected by analysis of the converted electric impulses. Through the use of computer of the detected brain waves, it is state of the art to graphically "map" the brain on the computer's cathode ray tube, i.e. CRT, to check for abnormalities relative to an appropriate reference data base.

EEG testing is not limited to detecting abnormalities in brain function. The technology is used in the therapeutic monitoring of the central nervous system (CNS) effective drugs such as, for example anti-epiletics, cerebrovascular compounds, psychotropics i.e. antidepressants, anxiolytics, antipsychotics, antihistamines and analgesics, etc for determining the effect such drugs have on the brain. EEG testing has also been used clinically to determine the CNS toxicity of peripheral drugs such as cardiovascular drugs, to select the proper psychotropic for a particular patient and/or to determine the development of a progressive cerebral illness by repetitive quantitative EEG testing.

As a research tool, EEG testing has been used to establish quantitive CNS effect of drugs after single and/or multiple doses; for classifying psychotopic properties of drugs; for predicting the "therapeutic window" of psychotropics; and for determining the potency of CNS-effective drugs and determining appropriate dose levels.

Prior art EEG systems are described in U.S. Pat. Nos. 3,518,986; 3,859,988; 4,202,352; 4,213,465; 4,214,591; 4,235,511; Re 30,502; 4,409,987; 4,411,273; 4,424,816 and 4,632,122. Despite the advancement and sophistication of the technology used in current EEG testing the area which appears to warrant more advancement is in electric impulse detection. Hardware used for electric impulse or brain wave detection normally includes some nineteen individual electrodes, particularly located about the scalp. The electrodes are specifically designed to make electrical contact with the subject's scalp or skin and the electric constant of the electrodes must be established on a comparatively uniform, consistent basis in order to obtain a true representation of the brain waves monitored. Placement of electrodes for EEG testing has been a function of measurements of the subject's head, taken by the technician conducting the test, in accordance with the International 10-20 system.

Example of prior art electrodes include those described in U.S. Pat. Nos. 2,872,926; 3,151,619; 3,170,459; 3,187,745; 3,295,515; 3,469,577; 3,528,408; 3,580,239; 3,602,216; 3,623,479; 3,669,110; 4,033,334; 4,051,842 and 4,632,122.

As a review of these patents will demonstrate, the state of the art relative to electrode design and placement for EEG systems has not advanced in step with the related hardware and software used in analyzing the EEG test results. For most electrode designs, location and placement of the individual electrodes are on a trial and error basis and consistency in placement of electrodes remains a problem. The securing of the plurality of electrodes to the patient's scalp is a cumbersome, messy and time consuming activity which most often requires a gross inconvenience to the patient and may require substantial training on the part of the technician. The amount of time required to properly locate and connect a set of electrodes at nineteen (19) different location on a patient's scalp, determined in accordance with the International 10-20 system can be substantial, often taking as long as thirty to forty-five minutes.

In most cases, the chances of locating electrodes in exactly the same positions on the scalp of the sam patient during repetitive testing, is difficult, problematic and highly unlikely, thus tending to adversely effect the reliability of the results of repetitive tests on the same patient. Moreover, the chances of obtaining and maintaining good, consistent electrical contact between the electrodes and the scalp at all multiple locations can prove difficult due to differences in skull size, shape and the amount and texture of hair cover of different patients or subjects.

A more recent development in the hardware relating to electrodes used in EEG tests includes the use of a headset, fitted with a plurality of electrodes, suitable for placement on the head of a patient or subject to be tested. The electrodes are mounted in the headset and are biased, by the use of resilient material, against the scalp of the patient. Independent positive orientation of each electrode mounted in a helmet is achieved by the use of a gas pressure system.

SUMMARY OF THE INVENTION

The present invention provides an improved electrode and EEG amplification system apparatus mounted in a headset or helmet in which self contained amplifiers are integrated into each electrode assembly mounted in a headset. Each amplifier includes a self contained battery system or is connected to an internal headset mounted common power source and switching or activation apparatus which drives an operational amplifier when the electrode is moved into contact with the scalp of the patient or subject being tested. Each operational amplifier may include an analog to digital (A/D) signal converter which has the advantage of providing a proportional digital output to a computer interface, as opposed to applying the analog signal representing the electric impulse or brain wave in essentially original form which then must be converted at the computer end.

The output of the amplifier of each electrode is fed, in parallel arrangement via an interface input into a computer. If the amplifier includes an A/D signal converter the outputs of the amplifiers will be a digital signal representing the brain wave detected. These signals then may be transmitted to the computer through a wireless signal transmitting system. If the amplifier does not include an A/D signal converter, the outputs of the amplifiers will be analog signal representations of the brain wave detected. In the latter case analog representations are fed into the input interface of a computer. Conversion of the analog signal into corresponding digital form may be required if the computer is digital in characteristic. It is apparent that analog computerization means may be used but the present state of the art tends to use digital computation means.

Large scale integration (LSI) chips may be used on which amplification circuitry has been imbedded. Such LSI chips are of a size that a chip may be housed in the electrode positioning hardware and the power source driving the amplifier may be a small battery, located convenient to the LSI chip. The LSI chip containing the operational amplifier may be encapsulated and a lead for applying the amplified signal may be fed from the output of the amplifier to an input interface.

OBJECTS OF THE INVENTION

It is an object of the invention to provide an improved electrode for use in an EEG system.

Another object is to provide an improved electrode system for detecting electric impulses or brain waves for use in an EEG system.

A further object is to provide an improved electrode for detecting and/or sensing electric impulses or brain waves of a subject in which an operational amplifier is integrated into the electrode assembly.

BRIEF DESCRIPTION OF THE DRAWINGS

These and other objects will become more apparent when reading the following detailed description of the invention in conjunction with the drawings in which.

DESCRIPTION OF THE PREFERRED EMBODIMENT

Figure 1:
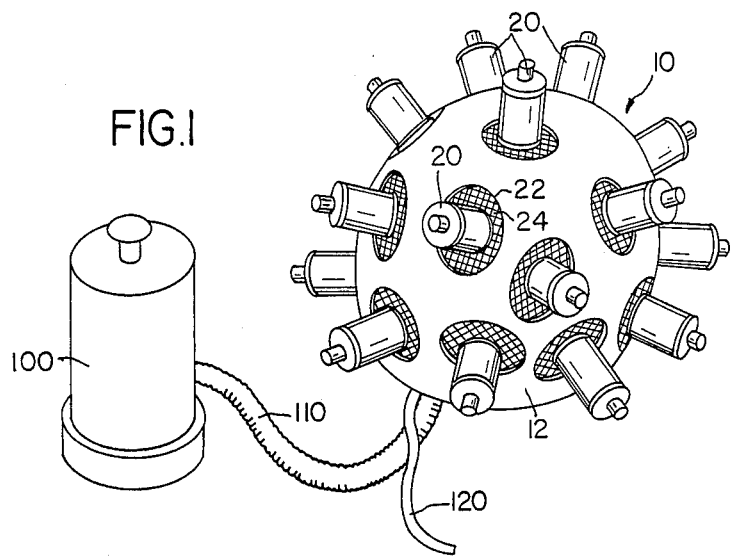
FIG. 1 is a perspective view of a headset or helmet with positioned electrodes of the present invention.
Figure 2:
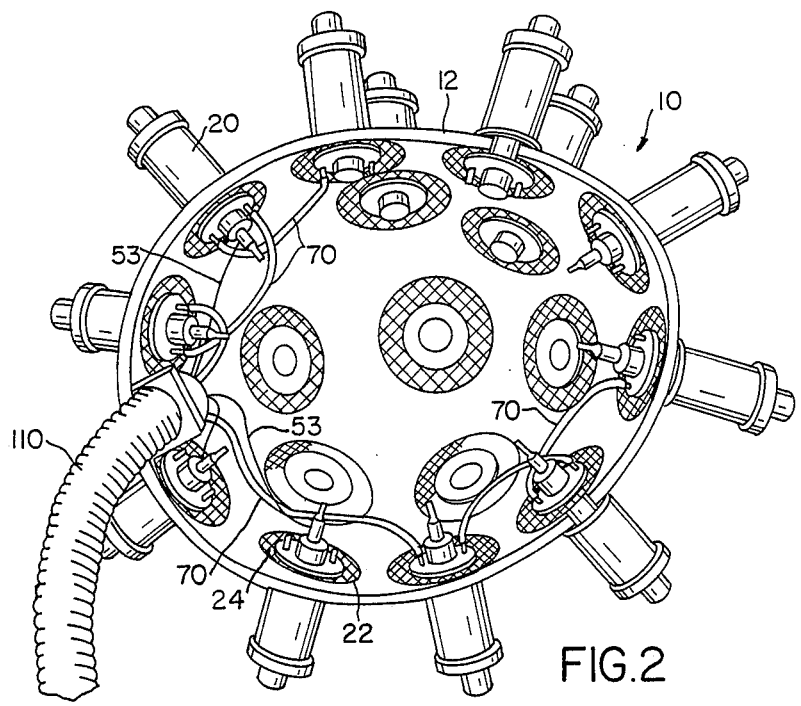
FIG. 2 is a view of the inside of the headset or helmet.

Referring to the drawings, FIGS. 1 and 2 illustrate a headset or helmet 10 into which a plurality of improved electrode assemblies of the present invention are mounted. The headset includes a helmet liner 12 with a plurality of electrode assemblies 20 placed or mounted at predetermined positions about the liner. The liner 12 may be fabricated from a rigid thermoplastic material and may be in the form so as to reassemble a modified version of a hockey, football or other type helmet.

Nineteen electrode assemblies are provided at fixed location about the headset and are positioned in accordance with standard electroenciphalographic procedures, i.e. International 10-20 system, for performing conventional EEG testing. In order to accommodate each of the electrode assemblies 20, a like number of apertures or mounting holes 22 are provided in the liner 12 at positions where the electrode assemblies are to be inserted or mounted. Each electrode assembly 20 is retained within its respective aperture and each electrode 50 is retained in its respective electrode assembly. The assembly 2 is retained by a resilient mesh 24 which encircles and supports the assembly, the mesh being adhesively bonded to the liner. By securing the electrode assembly 20 within the aperture 22 by use of the resilient mesh 24, or open elastic grid or web line support the positioning of each electrode assembly and its contained electrode 50 is automatically adjusted to accommodate subjects having skulls of different sizes and shapes. Because of the resilience of the mesh, and therefore the mounting of the electrode assembly, all that is required of the technician is to oscillate the electrode assembly so as to displace hair from the tip of the electrode 50, according better placement of the electrode 50 on the scalp. Using an electrolyte gel, good electrical contact ma be achieved between the electrode and the scalp with minimal pressure of the electrode tip against the scalp. An additional advantage of using a mesh 24 is that the open material permits ventilation, permitting passage of air through the liner making the headset more comfortable to wear for prolonged periods of time thereby according and/or reducing scalp perspiration and attendant problems thereof.

The resilient mesh may be replaced by other resilient material, if desired. It is however preferred that the electrode assemblies be mounted so that the electrode 50 in the electrode assembly 20 travels substantially perpendicular relative to the supporting shell at place of attachment of the assemblies to the shell with conformity of electrode tip contact being made in accordance with the International 10-20 system, but with sufficient pivotal movement of the electrode assembly in the mounting to ensure proper placement of the electrode tip on the scalp of the subject regardless of the variations in cranial size and/or contour.

Figure 3:
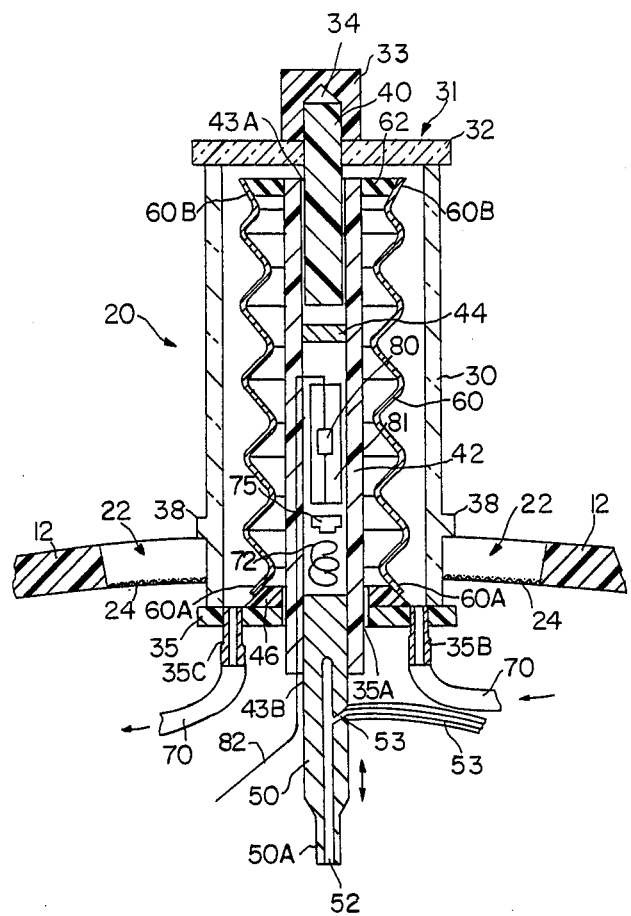
FIG. 3 is a sectional view of an electrode embodying the present invention, in its preferred form.

The preferred embodiment of the electrode assembly 20 is represented in more detail in FIG. 3, where the electrode assembly 20 includes an outer cylinder 30, preferably fabricated from a thermoplastic material such as, LUCITE, for example or polystyrene. The cylinder 30 is adapted to be located in the aperture 22 of the liner 12 and is captured therein by the resilient mesh 24 which is secured about the periphery of the cylinder, preferably adhesively bonded thereto, such that the lip 38 is above and protects the security between the shell of the cylinder and the resilient mesh. The cylinder is sealed at its upper end 31 by an end cap 32, with a top cap 33 provided in the end cap permitting access to the interior of the cylinder when the top cap 33 is removed. A post 40 is secured to the top cap 33 and extends downwardly into the interior of the cylinder 30.

It should be noted that in the preferred embodiment, practical elements of the electrode assembly may be constructed out of a plastic material. Where two plastic elements of the assembly are secured together, this security or securing may be accomplished by adhesively bonding the elements together or by welding the elements together, such as by thermal or sonic welding. In the case of the top cap 33, this cap is secured to the end cap 32 and, since access to the interior of the assembly is desirable, the end cap 32 may be bonded to the cylinder wall 30 and the top cap 33 may be threadedly coupled or secured to the end cap 32 for easy removal for removing the post 40, when desired. With the end cap 32 bonded to the wall of cylinder 30, the bottom cap 35 may be threadedly coupled or secured to the wall of cylinder 30 for permitting access to the internal structure and elements of the electrode assembly. Assembly of the electrode assembly so that coupled elements holding the assembly together are non-destructively disassembled provides an electrode assembly that is easily repairable in the event of breakdown.

The rod 40 coupled to the top cap 33 extends into the interior of the hollow piston rod 42 and aids in keeping the piston rod 42 in alignment, giving the upper ends of the hollow piston rod support. The hollow piston rod 42 has an upper end 43A which receives the rod 40 and reciprocates on the same, and a lower end 43B adapted to receive the electrode element 50. The electrode element 50 is mounted in the cylinder of rod 42 so as to have limited movement going into the cylinder 42 when the tip 50A of the electrode element 50 makes contact with the subject being tested. Travel of the electrode element is limited but sufficient to compress the spring 72 so that the battery 75 may come in contact with the top end of the electrode element and the LSI chip 80 mounted in the hollow cylinder of rod 42, below the plug 44.

It will be appreciated that the elements within the hollow cylinder of rod 42 are represented in the exploded view for purposes of clarity. The spring 72 is very small and sufficiently strong to separate the battery 75 from the electrode element 50 so as to maintain an open circuit when the electrode element is out of contact with the subject being tested. The LSI chip 80 is mounted on a substrate 81 which is held in place by the plug 44. A lead 82 is connected to the output of the amplifier LSI chip and conducts the amplified signals to the input interface of the computer (not shown).

The hollow rod 42 passes through the bottom cap 35 through an aperture 35A. The rod 42 floats in the aperture 35A but is held and prevented from full escape by the top shoulder 62 which is adhesively bonded to the rod 42 and to the upper end of the bellows 60 at 60B. The bottom end of the bellows 60 is bonded to a bottom shoulder 46 through which the hollow rod 42 passes.

The bottom cap 35 includes a gas; for example an inlet 35B and a gas outlet 35C. The gas pressure build up around the bellows 60 acts to drive the hollow rod 42 toward the bottom of the electrode assembly, thereby effectively extending or driving the electrode element 50 toward the center of the liner 12. The gas pressure system is connected in series connection among the electrode assemblies mounted in the headset so that gas pressure build up is uniform in each electrode assembly and, if there is a gas pressure failure in any one electrode assembly the gas pressure in all the connected electrode assemblies is adversely effected. This type of connection of the gas pressure system is preferred as such system is fail safe, that is, a drop in gas pressure in one electrode assembly causes a drop in gas pressure in all electrode assemblies in the same headset.

The bellows 60 is a flexible, compressible bellows, which returns to its original shape when the air pressure on both sides of the bellows is equalized. The bellows may be fabricated from synthetic or natural rubber or neoprene or other flexible material with memory characteristics. The interior of the bellows is open to atmospheric pressure through the aperture 35A which extends through the bottom cap 35 and shoulder 46. A positive pressure applied through the gas pressure lads 70 causes a collapsing of the bellows driving the rod 42 and its contents, toward the interior of the liner 12. As the hollow rod or cylinder 42 is driven toward the interior of the liner 12, which is toward the scalp of the person on whose head the headset is mounted, the rod carries with it the electrode 50, the spring 72, the battery 75, and the substrate 81 on which the LSI chip 80 is mounted. When the tip of the electrode 50 contacts the scalp back pressure from such contact with the scalp causes the electrode to stop its forward drive and ride back into the hollow rod 42 and overcome the bias of the spring 72. When the spring is compressed the electrical circuit normally held open by the spring 72 is completed thus turning on the amplifier on the LSI chip 80. Release of the gas pressure or equalization of the air pressure on both sides of the bellows causes the bellows to relax, causing the bellows to recover to its normal condition thereby withdrawing the hollow rod 42, and its contents back into the cavity of the electrode assembly. As the rod 42 recedes back into the cavity back pressure on the electrode 50 is removed and the spring 72 separates the battery from the electrode element breaking electrical connection thereby turning off the amplifier. The amplifier is turned on when electric connection is made between the one terminal of the battery and the electrode element and the other terminal of the battery and the amplifier input terminal on the substrate carrying the LSI chip.

The electrode element 50 is preferably fabricated from a good electrical conductor material, for example, copper or silver. The electrode element preferably includes a center aperture defining a channel or cavity 52. The channel is extended and opened along the body of the element and adapted to receive a tube 53. The tube 53 is connected to a source of electrolytic material 100 via the conduct 110. When the tip of the electrode element 50 is in contact with the scalp of the subject or patient being tested, a predetermined amount of an electrolytic material may be metered on to the surface of the scalp to aid in electrical contact between the electrode and the surface of the skin. Several electrolytic gels are commercially available but one preferred electrolytic material is ELECTRODE GEL marketed by Parker Laboratories, which is a buffered, non-corrosive electrolytic material It will be apparent that the battery 75 and spring 72 may be replaced by a biased switch and the battery may be mounted on the substrate 81 supporting the LSI chip 80. The biased switch would serve the purpose of opening and closing the circuit to turn the amplifier off and on respectively and as an electrical conductor, when closed, to conduct the electrical impulses or brain waves detected to the amplifier for amplification. The LSI chip may also include an analog to digital signal converter for converting the electrical impulse from analog form in to digital form.

The preferred embodiment of the invention having heretofore been described it will be apparent that changes and modification may be made, as will be apparent to one skilled in the art, without departing from the invention as defined in the appended claims.

What is claimed is:

1. An electrode assembly for detecting brain waves in the form of electric impulses, said assembly comprising:
   a. Electrode containing means including a cylindrical wall, a top cover and a bottom cover defining a hollow container, said bottom cover including an aperture therein;
   b. A hollow rod mounted in said container and extending from said aperture in said bottom cover, said hollow rod having upper and lower openings;
   c. an electrode element reciprocally received in said lower opening of said hollow rod;
   d. signal amplification means located in said hollow rod between said electrode element and said upper opening;
   e. a source of power positioned between said signal amplification means and said electrode element in said hollow rod and coupled to said signal amplification means for driving said signal amplification means;
   f. means between said electrode element and said signal amplification means for biasing said electrode element away from said signal amplification means, said biasing means subject to being overcome upon said electrode element being driven into said hollow rod, for turning on said amplification means; and,
   g. means responsive to pressure for partially driving said hollow rod out of said container and through said aperture for effecting contact of said electrode element with the scalp of a subject and for overcoming said biasing means for turning on said signal amplification means.

2. An electrode assembly as in claim 1 and in which said top cover includes an aperture therein and said assembly further includes:
   rod means extending through said aperture of said top cover and into the hollow of said hollow rod through said upper opening thereof for holding said hollow rod in alignment while said hollow rod is driven by said means responsive to pressure.

3. An electrode assembly as in claim 2 and in which said means responsive to pressure is a bellows coupled to an end of said hollow rod adjacent said upper opening and coupled to said bottom cover of said electrode containing means within said cylindrical wall and an air input extending through said bottom cover for applying air pressure into the space between said bellows and said cylindrical wall interior for compressing said bellows in response to air pressure in said space for driving said hollow rod partially out of said cylinder through the aperture in said bottom cover.

4. An electrode assembly as in claim 3 and in which said bellows is sealed for preventing air pressure applied to the outside thereof from entering the inside thereof and the interior of said bellows is open to atmospheric pressure.

5. An electrode assembly as in claim 1 and in which said signal amplification means is on a large scale integration chip and said chip is mounted on a substrate and said substrate is located in the hollow of said hollow rod between said electrode element and said upper opening.

6. An electrode assembly as in claim 1 and which said signal amplification means is on a large scale integration chip and said chip further includes analog to digital signal converter means.

7. An electrode assembly as in claim 1 in which said biasing means is a spring located between said electrode element and said signal amplification means.

8. An electrode assembly as in claim 7 and in which said source of power is a battery and said battery is located between said spring and said signal amplification means.

9. An electrode assembly as in claim 1 and in which said means for biasing is a normally open switch that closes an electrical circuit between said electrode element and said signal amplification means to turn on said amplification means when the bias is overcome by back pressure of said electrode element.

10. An electrode assembly as in claim 9 and in which said source of power is a battery mounted on a substrate supporting said signal amplification means.

* * * * *